(12) United States Patent
Kang et al.

(10) Patent No.: US 12,263,311 B2
(45) Date of Patent: Apr. 1, 2025

(54) METHOD FOR PROVIDING MENTAL MASSAGE TO HELP TREAT ANXIETY AND DEPRESSION, AND MASSAGE DEVICE

(71) Applicant: BODYFRIEND CO., LTD., Seoul (KR)

(72) Inventors: Woong Chul Kang, Gyeonggi-do (KR); A Ran Min, Seoul (KR); Jeong Hwan Lim, Seoul (KR)

(73) Assignee: BODYFRIEND CO., LTD., Seoul (KR)

( * ) Notice: Subject to any disclaimer, the term of this patent is extended or adjusted under 35 U.S.C. 154(b) by 832 days.

(21) Appl. No.: 17/282,773

(22) PCT Filed: Oct. 2, 2019

(86) PCT No.: PCT/KR2019/012969
§ 371 (c)(1),
(2) Date: Apr. 4, 2021

(87) PCT Pub. No.: WO2020/071819
PCT Pub. Date: Apr. 9, 2020

(65) Prior Publication Data
US 2021/0386963 A1 Dec. 16, 2021

(30) Foreign Application Priority Data
Oct. 4, 2018 (KR) .................. 10-2018-0118308

(51) Int. Cl.
*A61M 21/02* (2006.01)
*A61M 21/00* (2006.01)
(Continued)

(52) U.S. Cl.
CPC ............ *A61M 21/02* (2013.01); *G16H 20/70* (2018.01); *G16H 40/67* (2018.01); *G16H 50/20* (2018.01);
(Continued)

(58) Field of Classification Search
None
See application file for complete search history.

(56) References Cited

U.S. PATENT DOCUMENTS

| | | | |
|---|---|---|---|
| 6,702,767 B1 * | 3/2004 | Douglas | A61M 21/0094 601/16 |
| 2005/0131273 A1 * | 6/2005 | Asano | A61M 21/00 601/DIG. 13 |

(Continued)

FOREIGN PATENT DOCUMENTS

| | | |
|---|---|---|
| CN | 105267004 A | 1/2016 |
| CN | 107106047 A | 8/2017 |

(Continued)

*Primary Examiner* — Carrie R Dorna
(74) *Attorney, Agent, or Firm* — Bridgeway IP Law Group, PLLC; Sang Ho Lee; Hyun Woo Shin

(57) ABSTRACT

Disclosed are a method and a device for providing a mental massage to help treat anxiety and depression. According to one embodiment of the present disclosure, a massage device for providing a mental massage to help treat anxiety and depression is disclosed, the device including: a mental state determination unit for determining a mental state on the basis of a biosignal of a user; a mental massage pattern determination unit for determining a mental massage pattern on the basis of the determined mental state; and a mental massage provision unit for providing a massage on the basis of the mental massage pattern.

11 Claims, 11 Drawing Sheets

(51) Int. Cl.
*G16H 20/70* (2018.01)
*G16H 40/67* (2018.01)
*G16H 50/20* (2018.01)
*G16H 50/30* (2018.01)

(52) U.S. Cl.
CPC ..... *G16H 50/30* (2018.01); *A61M 2021/0022* (2013.01); *A61M 2021/0027* (2013.01); *A61M 2205/07* (2013.01); *A61M 2230/04* (2013.01); *A61M 2230/10* (2013.01); *A61M 2230/40* (2013.01); *A61M 2230/65* (2013.01)

(56) References Cited

U.S. PATENT DOCUMENTS

| | | | |
|---|---|---|---|
| 2006/0047179 A1* | 3/2006 | Graves | A61M 21/00 600/27 |
| 2006/0102171 A1* | 5/2006 | Gavish | A61B 5/4818 128/95.1 |
| 2008/0171914 A1* | 7/2008 | Ouwerkerk | A61M 21/00 600/27 |
| 2008/0269629 A1 | 10/2008 | Reiner | |
| 2018/0050170 A1* | 2/2018 | Kuhl | G16H 20/70 |
| 2018/0075764 A1 | 3/2018 | Bachani | |

FOREIGN PATENT DOCUMENTS

| | | |
|---|---|---|
| JP | H06225941 A | 8/1994 |
| JP | 2001-204694 A | 7/2001 |
| JP | 2002-224182 A | 8/2002 |
| JP | 2004355328 A | 12/2004 |
| KR | 10-0829328 B1 | 5/2008 |
| KR | 10-1858928 B1 | 5/2018 |
| KR | 10-2018-0103517 A | 9/2018 |
| KR | 10-1986956 B1 | 6/2019 |
| WO | 2008/009978 A1 | 1/2008 |
| WO | 2015/042579 A1 | 3/2015 |

\* cited by examiner (a)

| MENTAL MASSAGE PATTERN | (EMOTIONAL STATE) POSITIVE | NEGATIVE |
|---|---|---|
| (STRESS) LOW | MENTAL MASSAGE LEVEL 1 MODE | MENTAL MASSAGE LEVEL 2 MODE |
| MEDIUM | MENTAL MASSAGE LEVEL 2 MODE | MENTAL MASSAGE LEVEL 3 MODE |
| HIGH | MENTAL MASSAGE LEVEL 2 MODE | MENTAL MASSAGE LEVEL 3 MODE |

(b)

| Mental massage | Massage power | Massage depth | Aircell power | BLS time |
|---|---|---|---|---|
| Level 1 | 3-4 | 3-4 | 3 | FOUR MINUTES |
| Level 2 | 4-5 | 4-5 | 4 | FIVE MINUTES |
| Level 3 | 4-5 | 5-max | 5 | SIX MINUTES |

(c)

| (minutes) | 0 | 2 | 4 | 6 | 8 | 10 | 12 | 14 | 16 | 18 |
|---|---|---|---|---|---|---|---|---|---|---|
| Level 1 | | | | BLS | BLS | BLS | BLS | | | |
| Level 2 | | | | BLS | BLS | BLS | BLS | BLS | | |
| Level 3 | | | BLS | BLS | BLS | BLS | BLS | BLS | | |

● BLS : Bilateral Stimulation

FIG. 7

METHOD FOR PROVIDING MENTAL MASSAGE TO HELP TREAT ANXIETY AND DEPRESSION, AND MASSAGE DEVICE

TECHNICAL FIELD

The present disclosure relates to a method and massage device for providing a mental massage that helps heal anxiety and depression, and more particularly, to a method and massage device for providing a mental massage for restoring cerebral function and stabilizing the mind by providing bilateral stimulation to at least a part of the body according to a user's mental state.

BACKGROUND ART

In general, when a person's body is injured, pain is felt and a system for recovering wounds is activated. Thus, the pain subsides over time, and scars remain on the wounds. Unlike these wounds on the body, a mental wound leaves psychological trauma.

In 1980, as the diagnosis "post-traumatic stress disorder" was included in a formal diagnosis system, full-scale research on the psychological trauma began.

Thereafter, advances in brain science and technology have revealed how trauma disrupts a brain's nervous system and causes symptoms. After the trauma, the human's body enters a defense posture for survival. As the stress hormone "cortisol" is secreted and the autonomic nervous system is maximally activated, irritability, concentration problems, insomnia, and impulsive behavior appear even with minor stimulation.

Securing safety and providing a supportive environment is the first step in trauma recovery. Examples of treatments for restoring the limbic system and cerebral function to help return to daily life include eye movement desensitization and reprocessing (EMDR), hypnotherapy, cognitive behavioral therapy, and neurofeedback therapy, and drug treatment for stabilizing an unstable nervous system may be combined depending on the symptoms. When the trauma is healed, the direction of life can be prevented from being distorted or devastated due to aftereffects, and as a time in which the trauma is healed is shorter and continuous, a better effect can be achieved.

DISCLOSURE

Technical Problem

The present disclosure is directed to providing a method and a massage device that provide a mental massage to help heal anxiety and depression, which may provide a direct and physical bilateral stimulation according to a mental state of a user.

Technical Solution

A massage device which provides a mental massage to help heal anxiety and depression, the massage device including: a mental state determination unit that determines a mental state on the basis of a biosignal of a user; a mental massage pattern determination unit that determines a mental massage pattern on the basis of the determined mental state; and a mental massage provision unit that provides a massage on the basis of the mental massage pattern is disclosed.

A method of providing a mental massage that helps heal anxiety and depression, the method including: determining a mental state on the basis of a biosignal of a user; determining a mental massage pattern on the basis of the determined mental state; and providing a massage on the basis of the mental massage pattern is disclosed.

Advantageous Effects

A method and massage device for providing a mental massage to help heal anxiety and depression according to the embodiment of the present disclosure described above can stabilize the user's mental state by providing a physical and direct bilateral stimulation to at least a part of the human body.

Further, the method and massage device for providing a mental massage that helps heal anxiety and depression according to the embodiment of the present disclosure can maximize the stabilization of the user's mental state by providing bilateral stimulation through the massage device, and at the same time, by providing a professional voice narration tailored to the user's mental state.

In addition, the method and massage device for providing a mental massage to help heal anxiety and depression according to the embodiment of the present disclosure can provide a more precise customized mental massage by measuring and reflecting the mental state as a user's response to the mental massage and by providing a feedback massage matching a change of the user's mental state.

DESCRIPTION OF DRAWINGS

Various aspects are described with reference to the accompanying drawings, and herein, similar reference numerals are used collectively to refer to similar components. In the following embodiments, for the purpose of description, a plurality of specific details are presented to provide comprehensive understanding of one or more aspects. However, it is apparent that such aspect(s) may be implemented without these specific details. In other examples, widely-known structures and devices are illustrated in block diagrams to facilitate description of one or more aspects.

FIG. 7 is a related diagram for describing a level of the mental massage pattern determined according to a user mental state according to the embodiment of the present disclosure.

BEST MODE

Figure 1:
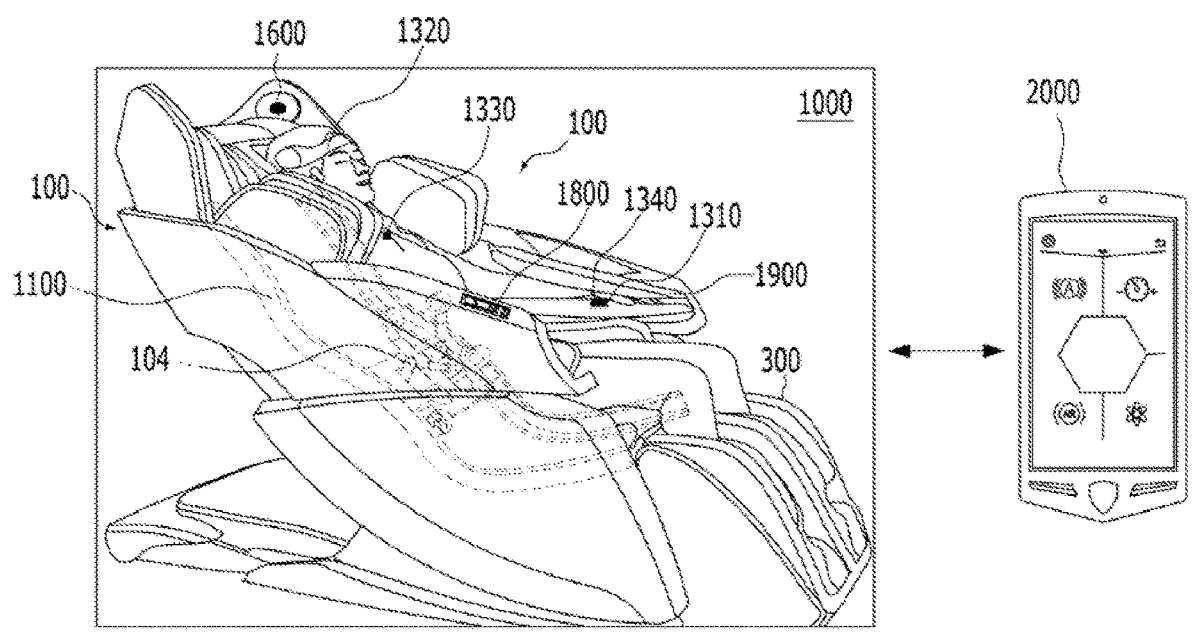
FIG. 1 is a view for describing a massage device according to an embodiment of the present disclosure.

A massage device and method which provide a mental massage to help heal anxiety and depression, the massage device including: a mental state determination unit that determines a mental state on the basis of a biosignal of a user; a mental massage pattern determination unit that determines a mental massage pattern on the basis of the determined mental state; and a mental massage provision unit that provides a massage on the basis of the mental massage pattern is disclosed.

[Modes of the Invention]

Objectives, features, and advantages of the present disclosure described above will become more apparent through the following embodiments related to the accompanying drawings. The following specific structure or functional descriptions are exemplified only to describe embodiments according to the concept of the present disclosure, the embodiments according to the concept of the present disclosure may be implemented in various forms, and the present disclosure should not be construed as being limited to the embodiments described in the present specification or application.

Since the embodiments according to the concept of the present disclosure may be variously changed and have various forms, specific embodiments are intended to be illustrated in the drawings and to be described in detail in the present specification or application. However, it should be understood that this is not intended to limit the embodiments according to the concept of the present disclosure to a specific disclosure, but includes all changes, equivalents, and substitutes included in the spirit and scope of the present disclosure.

Terms such as first and/or second may be used to describe various components, but the components are not limited to the terms. The terms are used only to distinguish one component from other component(s). For example, without departing from the scope of rights according to the concept of the present disclosure, a first component may be named a second component, and similarly, the second component may be named the first component.

It should be understood that, when a first component is referred to as being "connected" or "coupled" to a second component, the first component may be directly connected or coupled to the second component or a third component may be present between the first component and the second component. On the other hand, it should be understood that, when the first component is referred to as being is "directly connected" or "directly coupled" to the second component, a third component is not present therebetween. Other expressions used to describe the relationship between components, such as "between" and "directly between" or "adjacent" and "directly adjacent," should be interpreted in the same manner.

Terms used in the present specification are used only to describe specific embodiments and are not intended to limit the present disclosure. Singular expressions include plural expressions unless clearly otherwise indicated in the context. It should be understood that terms such as "include" or "have" used herein are intended to indicate the presence of features, numbers, steps, operations, components, parts, or combinations thereof that are described, and do not exclude in advance the possibility of the presence or addition of one or more other features, numbers, steps, operations, components, parts, or combinations thereof.

Unless otherwise defined, all terms used herein including technical or scientific terms have the same meanings as those commonly understood by those skilled in the art to which the present disclosure belongs. Terms defined in commonly used dictionaries should be interpreted as having the same meanings in the context of the related art, and may not be interpreted as ideal or excessively formal meanings, unless explicitly defined in the present specification.

In the present specification, an actuator means a component that may provide a driving force. For example, examples of the actuator may include an actuator, a linear actuator, an electronic actuator, a direct current (DC) actuator, an alternating current (AC) actuator, an electric actuator, and the like, and the present disclosure is not limited thereto.

In the present specification, a spiral rod may mean a straight member having a spiral-shaped groove and may be formed of a metal material. For example, the spiral rod may include a cylindrical rod having a spiral groove in the surface thereof. Further, the spiral rod may include a metal lead screw.

According to an embodiment of the present disclosure, a massage device may refer to a massage device including a body massage part and a leg massage part.

Terms "information" and "data" used in the present disclosure may be used interchangeably.

Sound sources in the present disclosure may include information in the form of a predetermined audio, including various types of music such as classical music, jazz music, instrumental music, and pop music, natural sounds such as sounds of water and sounds of birds, and binaural beats. Further, the binaural beat in the present disclosure may mean a specific type of audio information that may control brain waves.

Hereinafter, embodiments of the present disclosure will be described in detail with reference to the accompanying drawings.

FIG. 1 is a view illustrating a schematic configuration of a massage device 1000 according to the embodiment of the present disclosure.

The massage device 1000 according to the embodiment of the present disclosure may include a body massage part 100 that forms a region for accommodating at least a part of a user' body and massages the user's body, and a leg massage part 300 that massages a user's leg.

The body massage part 100 may provide a massage to at least a part of the user's body. The body massage part 100 may include a massage module 1700 that provides a massage function to at least a part of the user's body, an audio output module 1600 that provides an arbitrary type of audio output to the user, a main frame 1100 that constitutes the frame of the body massage part 100, and a user input unit 1800 that receives a predetermined type of input from the user.

Components included in the above-described body massage part 100 are merely exemplary embodiments, and the body massage part 100 may include various components in addition to the above-described components.

Further, the shape and structure of the massage device 1000 illustrated in FIG. 1 are merely illustrative, and various types of massage devices 1000 may be also included in the scope of the present disclosure without departing from the scope of rights defined by the appended claims of the present disclosure.

The body massage part 100 may form a space having a predetermined shape for accommodating the user. The body massage part 100 may have a space having a shape corresponding to the shape of the user's body. For example, as illustrated in FIG. 1, the body massage part 100 may be implemented as a seating type that may accommodate a user's whole body or a part of the body.

A portion of the body massage part 100 in contact with the ground may include a predetermined material for increasing a frictional force or a predetermined member (for example, a non-slip pad or the like) for increasing the frictional force, and may include wheels for enhancing the mobility of the massage device 1000.

At least a portion of the body massage part 100 may move in a sliding manner. For example, when the body massage part 100 starts a massage, at least a portion of the body massage part 100 may slidingly move forward. Further, the body massage part 100 may be inclined rearward. As a result, the body massage part 100 may provide the massage while being inclined rearward.

According to the embodiment of the present disclosure, the massage device 1000 may include at least one air cell.

The massage device 1000 may include an air supply part, and the air supply part may supply air to the air cell to inflate the air cell. The air supply part may be located inside the body massage part 100 and may be located in the leg massage part 300. Further, the air supply part may be located outside the massage device 1000.

The leg massage part 300 may provide a leg massage to the user.

For example, the leg massage part 300 may include a calf massage part that massages a user's calf and/or a foot massage part that massages a user's foot.

The leg massage part 300 may be adjusted in length according to user's body characteristics. For example, when a tall user uses the massage device 1000, the length of the calf is long, and thus the length of the leg massage part 300 needs to be lengthened. Further, when a small user uses the massage device 1000, the length of the calf is short, and thus the length of the leg massage part 300 needs to be shortened. Accordingly, the leg massage part 300 may provide a leg massage customized to a user's height.

The massage module 1700 may be provided inside the body massage part 100 to provide a predetermined type of mechanical stimulation to the user accommodated in the body massage part 100. As illustrated in FIG. 1, the massage module 1700 may move along the main frame 1100 provided inside the body massage part 100.

For example, a rack gear may be provided in the main frame 1100 of the body massage part 100, and the massage module 1700 may provide the mechanical stimulation to various portions of the user's body while moving along the rack gear. The massage module 1700 may include a ball massage part or a roller massage part, and the present disclosure is not limited thereto.

The main frame 1100 may constitute a frame of an internal configuration of the body massage part 100 and may be formed of a metal material or a plastic material. For example, the main frame 1100 may be formed of iron, an alloy, steel, or the like, but the present disclosure is not limited thereto, and the main frame 1100 may be formed of one of various hard materials.

According to the embodiment of the present disclosure, the massage device 1000 may include the audio output module 1600. The audio output module 1600 may be provided in various locations. For example, the audio output module 1600 may include a plurality of output units such as an upper audio output unit disposed in an upper end of a seat part, front audio output units attached to front ends of arm massage parts on the left and right sides of the seat part, and/or a rear audio output unit attached to a rear end of the arm massage part, and the present disclosure is not limited thereto. In this case, the audio output module 1600 may provide a surround sound with 5.1 channels, and the present disclosure is not limited thereto, According to the embodiment of the present disclosure, the user may control the massage device 1000 using a massage device control device 2000. The massage device control device 2000 may be connected to the massage device 1000 through wired communication and/or wireless communication.

The massage device control device 2000 may include a remote controller, a cellular phone, a personal digital assistant (PDA), or the like, but the present disclosure is not limited thereto, and the massage device control device 2000 may include various electronic devices that may be connected to the massage device 1000 through wired communication or wireless communication.

Figure 2:
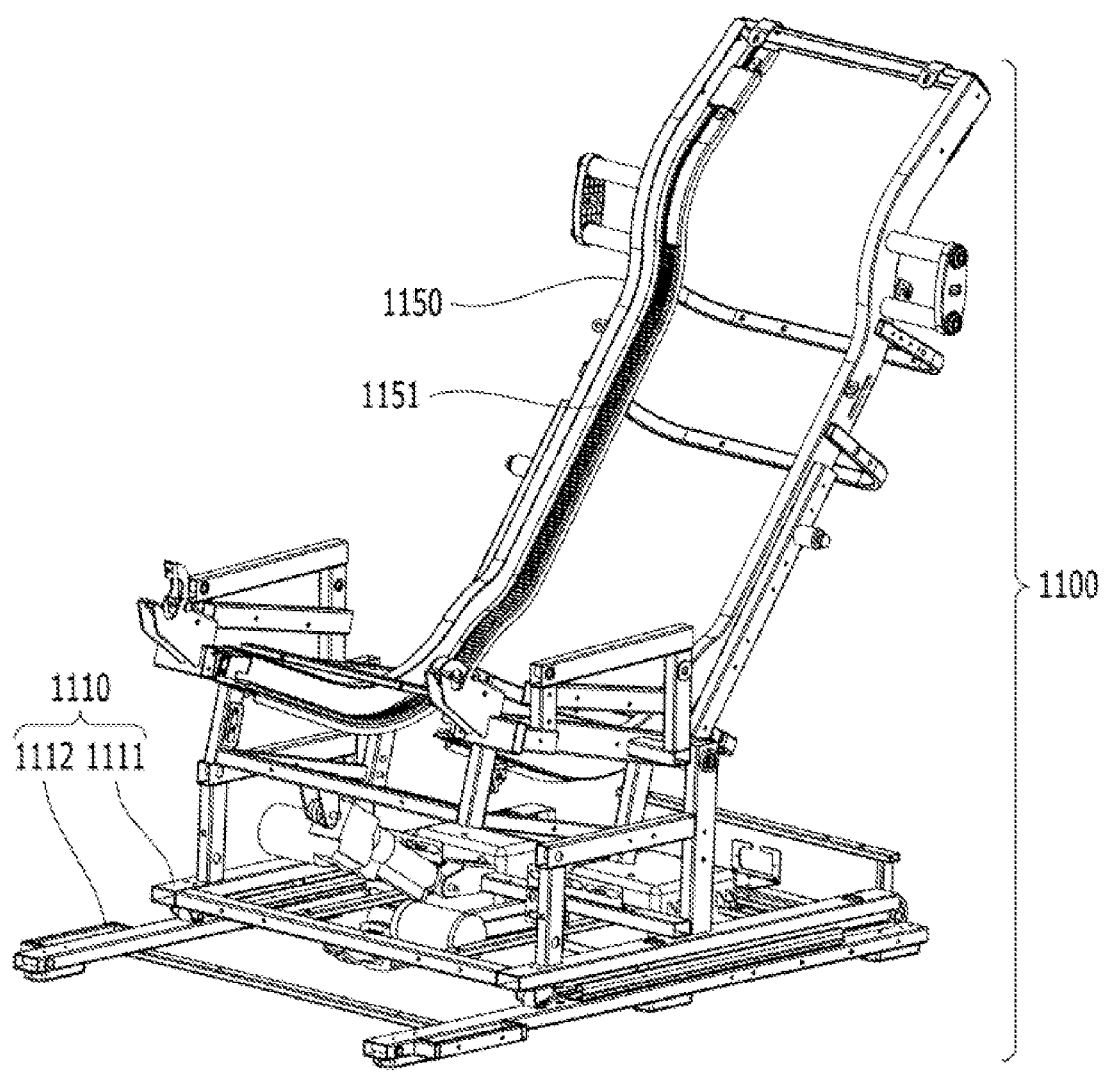
FIG. 2 is a view for describing a main frame according to the embodiment of the present disclosure.

FIG. 2 is a view for describing a main frame according to the embodiment of the present disclosure.

According to the embodiment of the present disclosure, the main frame 1100 may include an upper frame 1150 in which the massage module 1700 is provided and a base frame 1110 supporting the upper frame 1150.

At least a part of the upper frame 1150 may be provided with a rack gear 1151. The rack gear 1151, which is a member for guiding vertical movement of the body massage module 1700, may include a plurality of valleys and a plurality of peaks.

According to the embodiment of the present disclosure, the rack gear 1151 may be provided to face both sides of the upper frame 1150, and the body massage module 1700 may move along the rack gear 1151.

For example, the body massage module 1700 may include a gear engaged with the rack gear 1151, and as the gear is rotated by an actuator provided in the body massage module 1700, the body massage module 1700 may move upward or downward.

The rack gear 1151 may be formed of a metal material or a plastic material. For example, the rack gear 1151 may be formed of iron, steel, an alloy, reinforced plastic, melamine resin, phenolic resin or the like, and the present disclosure is not limited thereto.

The upper frame 1150 may be implemented in various shapes. For example, the upper frame 1150 may be classified into an S frame, an L frame, an S&L frame, and a double S&L frame according to the shape thereof, and the present disclosure is not limited thereto.

The S frame means a frame in which at least a part of the upper frame 1150 has a curved shape like "S." The L frame means a frame in which at least a part of the upper frame 1150 has a curved shape like "L," the S&L frame means a frame in which at least a part of the upper frame 1150 has both the curved shape like "S" and the curved shape like "L", and the double S&L frame means a frame in which at least a part of the upper frame 1150 has the curved shape like "L" and two curved shapes like "S."

The base frame 1110 means a part supporting the upper frame 1150 of the main frame 1100 and in contact with the ground. The base frame 1110 may include an upper base frame 1111 and a lower base frame 1112.

The upper base frame 1111 may support the upper frame 1150, and the lower base frame 1112 may be in contact with the ground. Further, the upper base frame 1111 may be located in contact with the lower base frame 1112.

According to the embodiment of the present disclosure, the upper base frame 1111 may move along the lower base frame 1112. For example, the upper base frame 1111 may slidingly move forward or rearward along the lower base frame 1112. In this case, the upper frame 1150 may be connected to the upper base frame 1111 and move according to the movement of the upper base frame 1111.

For example, when the upper base frame 1111 moves forward, the upper frame 1150 may also move forward, and when the upper base frame 1111 moves rearward, the upper frame 1150 may also move rearward. Accordingly, the sliding movement of the body massage part 100 may be allowed.

In detail, in order to allow the movement of the upper base frame 1111, moving wheels may be provided at a lower part of the upper base frame 1111. Further, guide members that can guide the moving wheels may be provided at an upper part of the lower base frame 1112. As the moving wheels provided at the upper base frame 1111 move along the guide members provided at the lower base frame 1112, the forward movement or rearward movement of the upper base frame 1111 may be allowed.

According to another embodiment of the present disclosure, the massage device 1000 may not provide a sliding function, and in this case, the base frame 1110 may not be divided into upper and lower frames.

Figure 3:
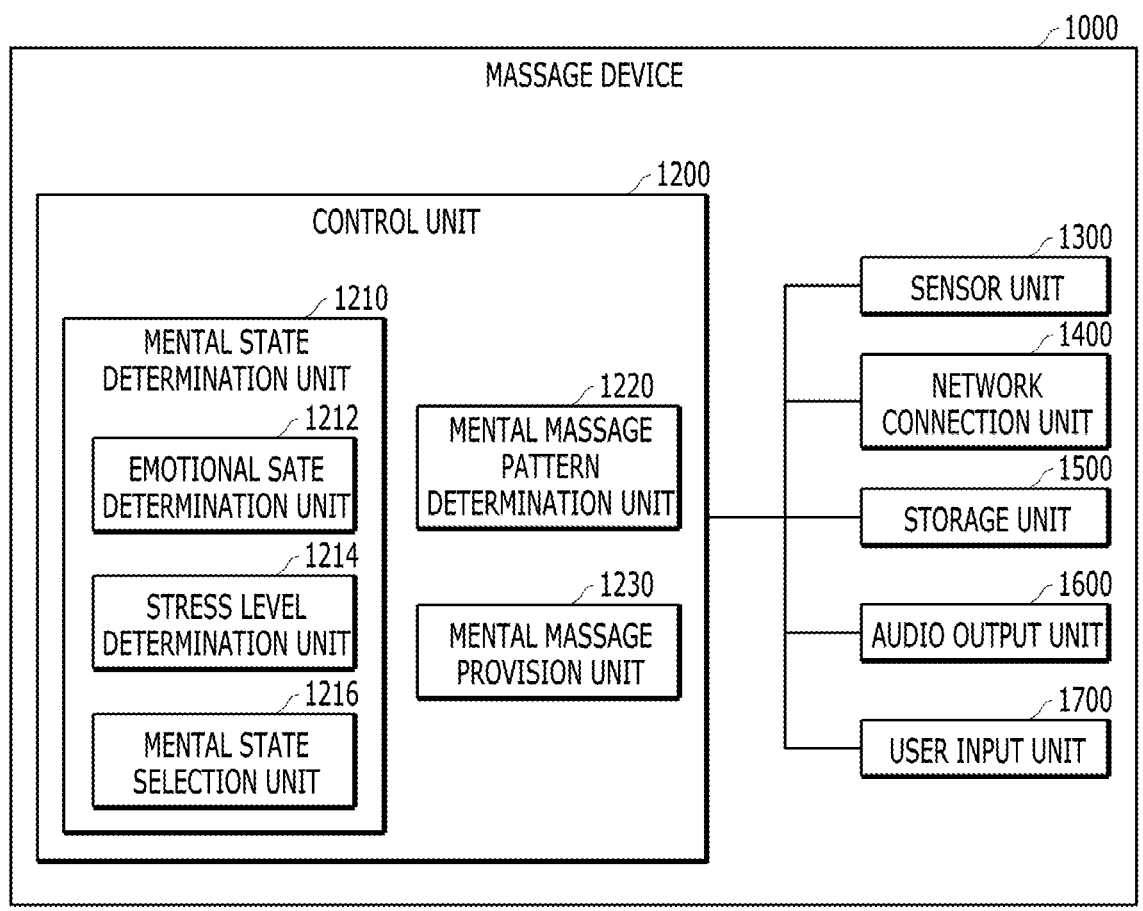
FIG. 3 is a view for describing components of the massage device according to the embodiment of the present disclosure.

FIG. 3 is a view illustrating components of the massage device 1000 according to the embodiment of the present disclosure.

According to the embodiment of the present disclosure, the massage device 1000 may include at least one of a control unit 1200, a sensor unit 1300, a network connection unit 1400, a storage unit 1500, an audio output module 1600, and a user input unit 1700.

The control unit 1200 may control the operation of the massage device 1000. The control unit 1200 may be implemented as one processor or a plurality of processors. When the control unit 1200 is implemented as the plurality of processors, at least some of the plurality of processors may be located at a physically spaced distance. Further, the control unit 1200 is not limited thereto and may be implemented in various ways.

According to the embodiment of the present disclosure, the control unit 1200 may control the operation of the massage device 1000. For example, the massage device 1000 may include a plurality of actuators, and the massage device 1000 may control the operation of the plurality of actuators to control the operation of the massage device 1000. For example, the massage device 1000 may include at least one of a moving actuator for the massage module 1700, at least one actuator included in the massage module, a back angle actuator, a leg angle actuator, a foot massage actuator, a leg length adjustment actuator, and a sliding actuator, and the control unit 1200 may control these actuators to control the operation of the massage device 1000.

The moving actuator for the massage module is an actuator that enables the vertical movement of the massage module 1700, the massage module 1700 may move along the rack gear by the operation of the moving actuator for the massage module 1700.

The back angle actuator is an actuator that adjusts the angle of a part of the massage device 1000 with which a user's back is in contact, and the back angle of the massage device 1000 may be adjusted by the operation of the back angle actuator.

The leg angle actuator is an actuator that adjusts an angle of the leg massage part 300 of the massage device 1000, and an angle between the leg massage part 300 and the body massage part 100 may be adjusted by the operation of the leg angle actuator.

The foot massage actuator refers to an actuator that operates a foot massage module included in the leg massage part 300. The massage device 1000 may provide a foot massage to the user using the foot massage actuator.

At least one actuator may be included in the massage module 1700, and the control unit 1200 may provide various massage operations by operating at least one actuator. For example, the control unit 1200 may operate at least one actuator included in the massage module 1700 to provide a tapping massage, a kneading massage, or the like, but the present disclosure is not limited thereto, and the control unit 1200 may provide various massages.

The leg length adjustment actuator refers to an actuator that adjusts the length of the leg massage part 300. For example, the control unit 1200 may utilize the leg length adjustment actuator to adjust the length of the leg massage part 300 according to the user, and as a result, the user may receive a massage suitable for his/her body shape.

The sliding actuator enables a sliding operation of the massage device 1000. For example, a horizontal upper base frame 1114a may be moved forward or rearward by the operation of the sliding actuator, and as a result, the upper frame connected to the horizontal upper base frame 1114a may be moved forward or rearward.

The sensor unit 1300 may acquire various pieces of information using at least one sensor. The sensor unit 1300 may be provided as a sensor using measuring means using pressure, electric potential, and optics. For example, the sensor may include a pressure sensor, an infrared sensor, a light emitting diode (LED) sensor, a touch sensor, and the like, but the present disclosure is not limited thereto.

Further, the sensor unit 1300 may include a biometric information acquisition sensor. The biometric information acquisition sensor may acquire fingerprint information, face information, voice information, iris information, weight information, electrocardiogram information, body composition information, or the like, but the present disclosure is not limited thereto, and the biometric information acquisition sensor may acquire various pieces of biometric information.

According to another embodiment of the present disclosure, the massage device 1000 may detect a contact area and/or a contact position with the user through the sensors. Further, the massage device 1000 may acquire shoulder position information of the user through the sensor unit 1300. Further, the massage device 1000 may provide a customized massage based on the acquired information. For example, when the massage device 1000 provides a shoulder massage, the massage device 1000 may recognize the position of a user's shoulder on the basis of the acquired information through the sensor unit 1300 and may provide the shoulder massage to the user according to the recognition result.

In particular, the sensor unit 1300 according to the embodiment of the present disclosure may be provided with at least one biometric sensor that obtains a user's biosignal. The biometric sensor may include at least one of an electro-dermal activity (EDA) sensor, an electroencephalography (EEG) sensor, a respiration sensor, and a blood volume pulse (BVP) sensor.

An EDA sensor 1310 may acquire a biosignal related to a user's stress level by measuring EDA known as a galvanic skin response of the human body. The EDA sensor 1310 may be mounted in a part that is easy to contact the skin of the user seated in the massage device 1000, for example, in a part inside an arm massage part 1900, corresponding to at least one among the wrist, the back of the hand, and the palm.

The EEG sensor may acquire a biosignal related to a sleep disorder caused by depression and neuropsychiatric disorders. The EEG sensor may be provided as an EEG measurement device 1320 connected to the massage device 1000 through wired/wireless communication in the form of a headset.

The respiration sensor may acquire a respiration pattern for measuring the degrees of anger, stimulation, and anxiety. As an example, the respiration sensor may be mounted on a user's clothes through a clip 1330 in a wearable form or may be mounted on one side of a shoulder air cell adjacent to a user's chest or one side of the body massage part 100 corresponding to the chest.

A BVP sensor 1340 may acquire a biosignal related to blood flow, a change in heart rate, and impulsiveness, and for this purpose, may be provided as a sensor the allows light to pass through the skin so as to measure a change in blood volume. The BVP sensor may be mounted on a part that is easy to contact the skin of the user seated in the massage device 1000, for example, a part inside the arm massage part 1900, corresponding to at least one among the wrist, the back of the hand, and the palm.

The signals measured by the above-described biometric sensors may be transmitted to the module inside the massage device 1000, an external massage device, and/or a user terminal 2000 through a predetermined type of network through the network connection unit 1400.

The user input unit 1800 may receive, from the user, a command related to motion control of the massage device 1000, and the user input unit 1800 may be implemented in various forms. For example, the user input unit 1800 may be provided in the body massage part 100 or may be provided in the leg massage part 300, but the present disclosure is not limited thereto.

The massage device 1000 may acquire various commands from the user through the user input unit 1800. For example, the massage device 1000 may receive predetermined commands for selection of a massage module, selection of a massage type, selection of a massage intensity, selection of a massage time, selection of a massage site, selection of a position and operation of the body massage part 100, selection of power on-off of the massage device 1000, selection of whether to operate a heating function, and selection related to sound source reproduction, but the present disclosure is not limited thereto.

In particular, the massage device 1000 according to the embodiment of the present disclosure may provide a user interface through which the user may select a mental massage mode. For example, a list of medical massages of various modes may be arranged through the massage device control device 2000, and a screen may be provided through which the user may select a mental massage mode among the list of the medical massages. The medical massage mode may include at least one of a concentration mode, a meditation mode, a recovery mode, a stretching mode, a sleep mode, a vitality mode, a golf mode, a hip-up mode, a student mode, a zero gravity mode, a growth and development promotion mode, and a mental massage mode.

When the user selects the mental massage mode, the description of the effect of the mental massage mode may be provided together with a guide message "We provide a customized mental massage after measuring your mental state" through the massage device control device 2000 or a speaker.

Further, in order to measure the mental state, the user may be guided through a method of using the sensor equipment provided in the massage device 1000. For example, at least one notice among the headset-type EEG measurement device 1320 should be worn on the head, the arm should be seated on the arm massage part 1900 equipped with at least one of the EDA sensor 1310 and the BVP sensor 1340, and the clip 1330 including the respiration sensor should be mounted on clothing adjacent to the chest may be provided.

In addition, the massage device control device 2000 may provide information on the measurement result of the mental state of the user. For example, the measurement result of the mental state may include information on a stress level and an emotional state of the user. The contents of the interface and the information provision are merely one example, and the present disclosure is not limited thereto.

According to the embodiment of the present disclosure, the user input unit 1800 may include buttons in the form of hot keys and/or selection buttons for executing selection, cancellation, and input of a direction according to a preset user setting function, a self-preset function, or the like.

The user input unit 1800 may be implemented as a key pad, a dome switch, a (positive pressure/capacitive) touch pad, a jog wheel, a jog switch or the like, and the present disclosure is not limited thereto. Further, the user input unit 1800 may acquire a command through user's utterance on the basis of a speech recognition technology.

According to the embodiment of the present disclosure, the user input unit 1800 may include a display for displaying an operational state of the massage device 1000, a user's current state, or the like. In this case, the display may include at least one of a liquid crystal display (LCD), a thin film transistor-liquid crystal display (TFT LCD), an organic light emitting diode (OLED) display, a flexible display, and a three-dimensional (3D) display, and the present disclosure is not limited thereto.

The audio output module 1600 may provide an audio output having a predetermined form to the user. For example, the audio output module 1600 may provide brain stimulation to the user by outputting, to the user, a sound source and/or a binaural beat optimized for a massage pattern provided by the massage device 1000. The audio output module 1600 may output an acoustic signal received through a network (not illustrated) or stored in an internal/external storage medium (not illustrated). For example, the audio output module 1600 may output a sound source according to control of the user terminal 2000 through a network connection (for example, a Bluetooth connection or the like) with the user terminal 2000. Further, the audio output module 1600 may output an acoustic signal having a predetermined form generated in connection with the operation of the massage device 1000.

The massage device 1000 according to the embodiment of the present disclosure may include the network connection unit 1400. The network connection unit 1400 may communicate with a module inside the massage device 1000, an external massage device and/or the user terminal 2000 through a network having a predetermined form. The network connection unit 1400 may include a wired/wireless connection module for network access. Examples of a wireless connection technology may include a wireless local area network (WLAN), wireless broadband (Wibro), world interoperability for microwave access (WiMAX), high speed downlink packet access (HSDPA) and the like. Examples of a wired connection technology may include a digital subscriber line (XDSL), fibers to the home (FTTH), power line communication (PLC), and the like. Further, the network connection unit may include a short range communication module and transmit/receive data to/from a predetermined device/terminal located within a short distance. For example, examples of the short range communication technology may include Bluetooth, radio frequency identification (RFID), infrared data association (IrDA), ultra wideband (UWB), ZigBee, and the like, and the present disclosure is not limited thereto.

The storage unit 1500 may store various pieces of information related to the massage device 1000. For example, the storage unit 1500 may include massage control information and include personal authentication information, and the present disclosure is not limited thereto.

In particular, the storage unit 1500 according to the present disclosure may store, for each user, information on the mental state determined for the user and information on the massage pattern determined for the user. Further, the storage unit 1500 may store, for each user, a change in mental state and a change history of a mental massage pattern.

Figure 4:
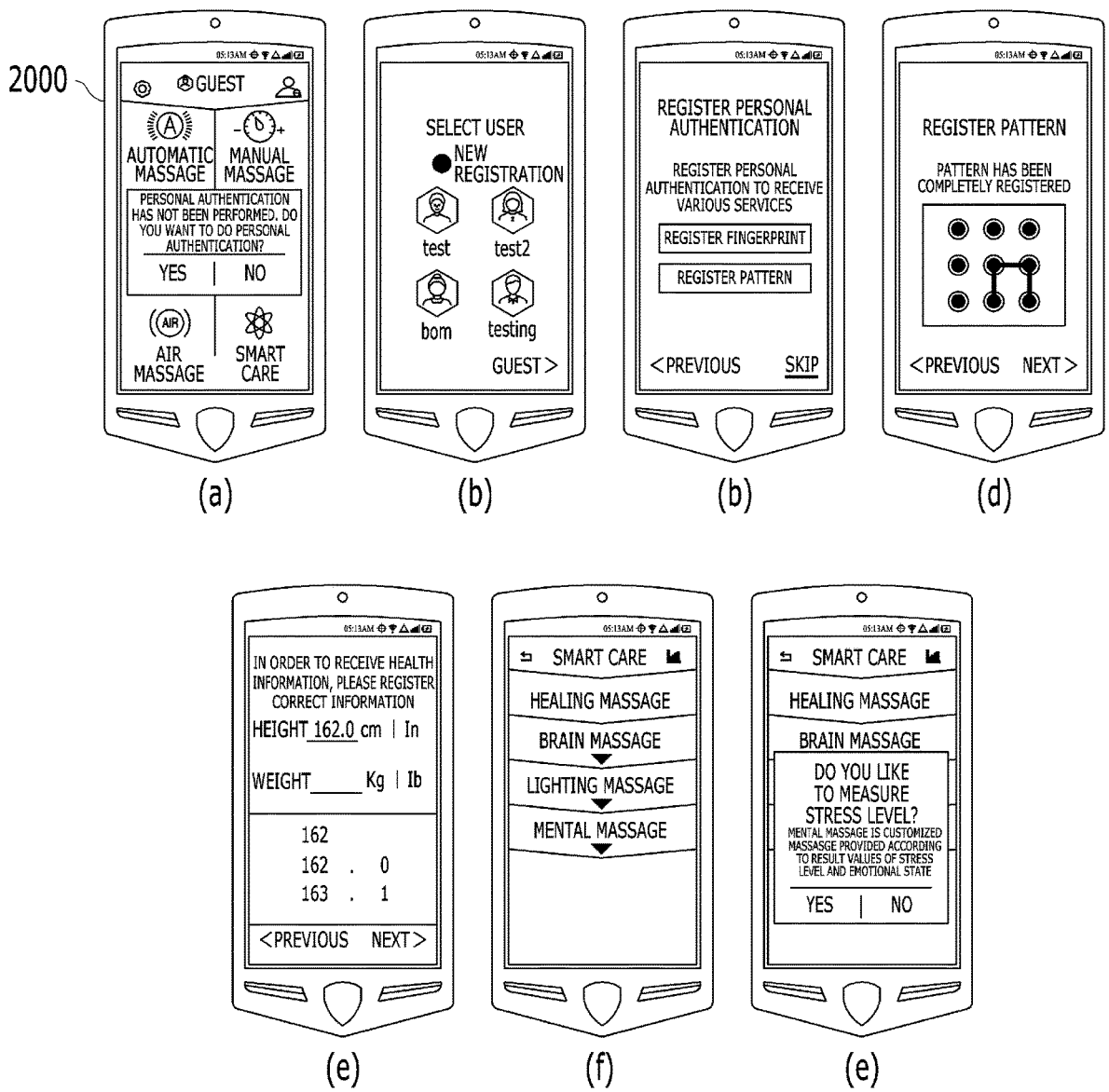
FIG. 4 illustrates an example of an execution screen of a control device of the massage device according to the embodiment of the present disclosure.

To this end, as illustrated in FIG. 4, first, at least one execution screen among a user personal authentication execution screen (a) using the massage device 1000 through the massage device control device 2000, a user selection and new user registration screen (b), a fingerprint registration or pattern registration screen (c or d) for registering personal authentication when a new user is registered, a screen (f) for selecting a mental massage, and a mental state measurement guide screen (g) when the mental massage is selected may be provided as a user interface for user information registration, authentication and mode selection.

Information on the mental massage pattern may include at least one of (1) the total time of the massage provided to the user according to a specific mode, (2) a massage type indicating the type of mechanical stimulation provided by the massage device, (3) a massage region or massage location according to the specific mode, (4) a massage intensity indicating the intensity of the mechanical stimulation provided by the massage device, and (5) an operation method and an operation sequence of the massage device.

Figure 5:
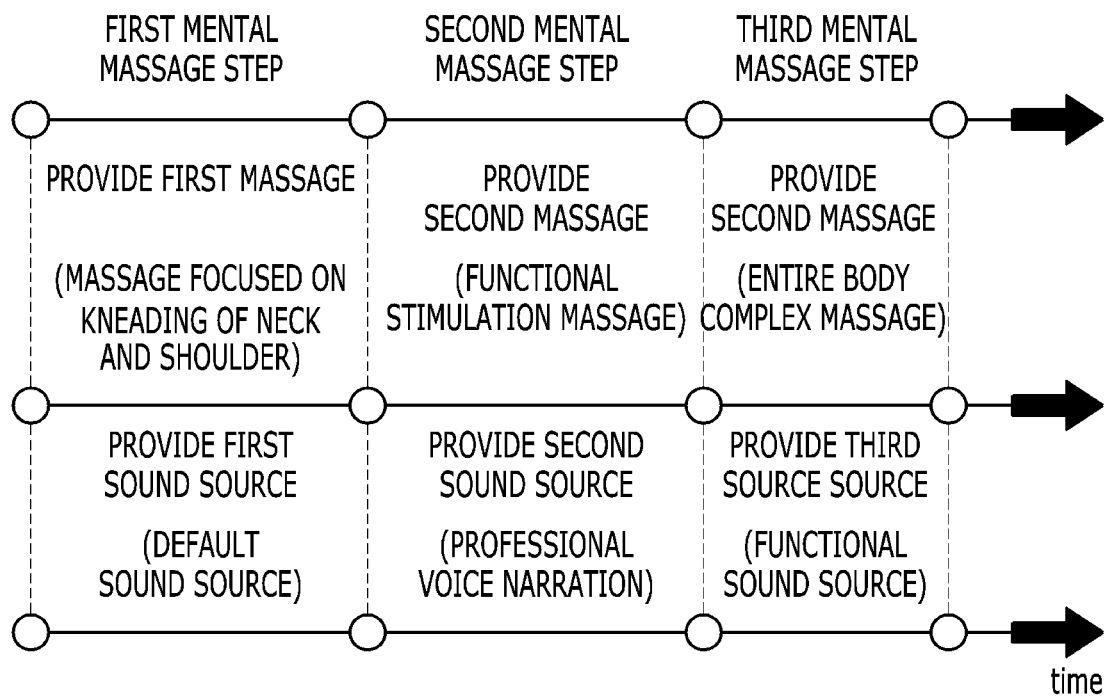
FIG. 5 is a view for describing a basic step of a mental massage pattern according to the embodiment of the present disclosure.

As illustrated in FIG. 5, the mental massage pattern according to the present disclosure may basically include a first mental massage step, a second mental massage step, and a third mental massage step.

In the first mental massage step that is a step of starting the mental massage, a first massage may be provided which is focused on massaging the neck and the shoulders, in the second mental massage step that is a step of providing the mental massage in earnest, a second massage may be provided which provides functional stimulation, and in the third massage step that is a step of finishing the mental massage, a complex third massage may be provided to the whole body. The functional stimulation will be described below with reference to FIGS. 7 and 8.

In addition, in the first mental massage step, an intro sound source set as a default may be provided, in the second mental massage step, the functional stimulation may be provided while professional voice narration is provided, and in the third mental massage step, an outro sound source set as a default may be provided.

The storage unit 1500 may be implemented through a non-volatile storage medium that may continuously store predetermined data. For example, the storage unit 1500 may include a storage device based on a flash memory and/or a battery backup memory as well as a disk, an optical disk, and a magneto-optical storage device, and the present disclosure is not limited thereto.

Further, the storage unit 1500 may include a memory. The memory may mean a volatile storage device, such as a random access memory (RAM) such as a dynamic RAM (DRAM) and a static RAM (SRAM), which is a primary storage device directly accessed by a processor, and in which stored information is instantly erased when power is turned off, and the present disclosure is not limited thereto. Such a memory may be operated by the control unit 1200.

The control unit 1200 may include a mental state determination unit 1210, a mental massage pattern determination unit 1220, and a mental massage provision unit 1230.

The mental state determination unit 1210 may determine the mental state on the basis of the user's biosignal, the mental massage pattern determination unit 1220 may determine the mental massage pattern on the basis of the determined mental state, and the mental massage provision unit 1230 may provide a massage on the basis of the mental massage pattern.

In detail, the mental state determination unit 1210 may include an emotional state determination unit 1212, a stress level determination unit 1214, and a mental state selection unit 1216.

The emotional state determination unit 1212 may determine the emotional state of the user on the basis of the biosignal of the user. To this end, a first biosignal may be acquired through at least one of the EEG measurement device 1320 including the EEG sensor, the clip 1330 including the respiration sensor, and the BVP sensor 1340.

The stress level determination unit 1214 may acquire a second biosignal through the EDA sensor.

The mental state selection unit 12216 may extract a first feature and a second feature by analyzing the first biosignal and the second biosignal and determine the mental state of the user on the basis of the first feature and the second feature. The first feature and the second feature may be related to a first standard and a second standard for determining a mental state, respectively. Here, the analysis may be a predefined analysis and determination algorithm based on a predefined or mental state model.

The mental state selection unit 1216 may pre-process each biosignal before extracting the feature from each biosignal. For example, the mental state selection unit 1216 may perform signal pre-processing such as peak detection, noise removal, and filtering.

In the embodiment, the mental state selection unit 1216 may extract the first feature related to the emotional state from the first biosignal, classify the emotional state into a positive state or a negative state on the basis of the extracted first feature, extract the second feature related to a stress level from the second biosignal, classify the stress level into a high state, a middle state, and a low state on the basis of the extracted second feature, determine in which state of a mental model a current mental state of the user is included, and thus determine the current mental state of the user.

To this end, the emotional state and the stress level are quantified on the basis of the first feature and the second feature, the quantified emotional state and the quantified stress level are classified, which region of a plurality of regions set by the mental state model the current state is included is determined, and thus the current mental state of the user may be determined. Here, the emotional state may mean an index indicating whether the emotion is positive or negative, and the stress level may mean a stress index of the user.

Figure 6:
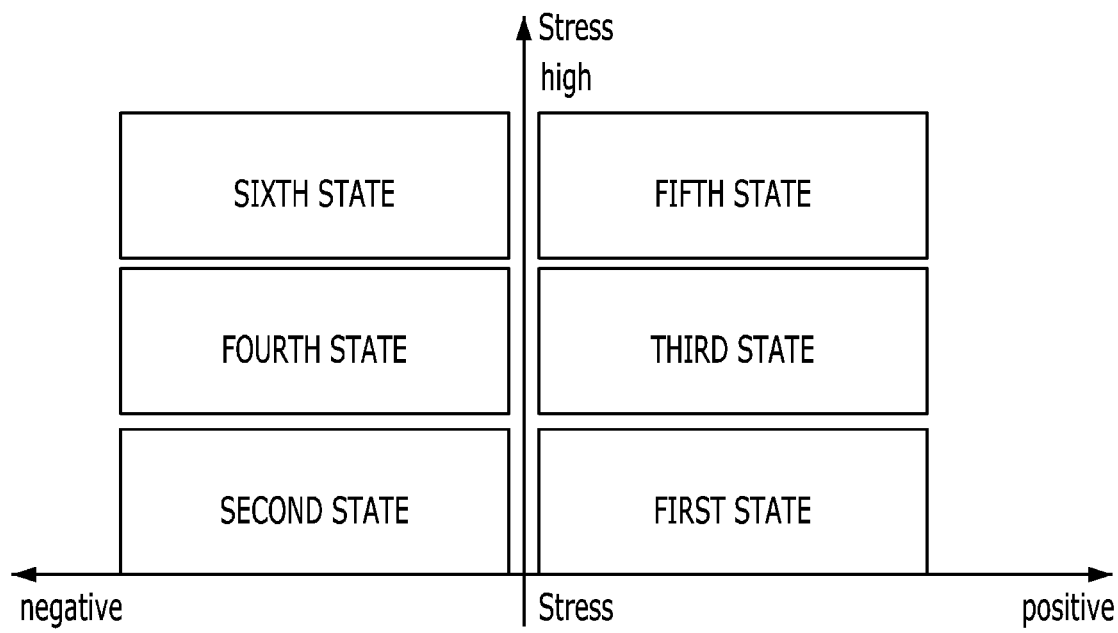
FIG. 6 illustrates an example of a mental state model according to the embodiment of the present disclosure.

In the mental state model of the present disclosure illustrated in FIG. 6, a state in which the emotional state is positive and the stress level is low may be classified as a first state, a state in which the emotional state is negative and the stress level is low may be classified as a second state, a state in which the emotional state is positive and the stress level is medium may be classified as a third state, a state in which the emotional state is negative and the stress level is medium may be classified as a fourth state, a state in which the emotional state is positive and the stress level is high may be classified as a fifth state, and a state in which the emotional state is negative and the stress level is high may be classified as a sixth state. The above-described mental state model is an exemplary mental state model, and the determination of the mental state of the present disclosure may be performed using a different mental state model.

For example, the mental state determination unit 1210 may determine that the mental state of the user is the third state, when the classified emotional state is positive and the classified stress level is medium.

The above-described embodiment is merely illustrative, and the mental state determination unit 1210 may determine the current mental state of the user on the basis of the first feature and the second feature using various standards and methods according to the types and characteristics of the extracted first feature and the extracted second feature.

FIG. 7 is a related diagram for describing a level of the mental massage pattern determined according to a user mental state according to the embodiment of the present disclosure.

The mental massage pattern determination unit 1220 may determine the level of the mental massage pattern provided to the user on the basis of the determined mental state of the user. In the embodiment, the level of the mental massage pattern may be classified into three levels.

Further, the intensity of the massage, the depth at which the massage module 1770 pushes a backbone, the strength of the air cells 110, 112, 140, 142, 320, 322, 1910, and 1920, and the time during which the functional stimulation is provided may be differently set according to the level of the mental massage pattern.

As illustrated in FIG. 7A, in the case of a model in which the level of the mental massage pattern is classified into three states, the mental massage pattern determination unit 1220 may determine a first level mental passage pattern when the mental state is the first state (emotional state is positive and stress level is low), determine a second level mental massage pattern when the mental state is the second state (emotional state is negative and stress level is low), determine the second level mental massage pattern when the mental state is the third state (emotional state is positive and stress level is medium), determine a third level mental massage pattern when the mental state is the fourth state (emotional state is negative and stress level is medium), determine the second level mental massage pattern when the mental state is the fifth state (emotional state is positive and stress level is high), and determine the third level mental massage pattern when the mental state is the sixth state (emotional state is negative and stress level is high).

Referring to FIG. 7B, when the emotional state of the user is determined as the negative state, the mental massage pattern determination unit 1220 may determine the level of the mental massage pattern to be relatively higher than that of the positive state.

Further, when the stress level of the user is determined as being larger than or equal to a threshold, the mental massage pattern determination unit 1220 may determine the level of the mental massage pattern to be relatively higher than a case in which the stress level is smaller than the threshold.

As the level of the mental massage pattern becomes higher, the depth at which the massage module 1770 pushes the backbone may become deeper, the strength of the air cells may become stronger, and the time during which the functional stimulation is provided may become longer. Here, the strength of the air cells may be adjusted according to the amount of air injected into the air cells.

In particular, in particular, the functional stimulation of the present disclosure may mean bilateral stimulation provided to the user on the basis of the bilateral stimulation theory. The bilateral stimulation theory is a technique in which bilateral stimulation is provided to at least a part of the body, a data processing method of the brain is tuned in parallel with brain (particularly, limbic system) use activation, and which is thus helpful in resolving psychological trauma.

As one of the common bilateral stimulation techniques, for example, in eye movement desensitization and reprocessing (EMDR), in order to treat a depressed patient, the pupils of a patient are induced to move horizontally leftward and rightward, and at the same time, a doctor reminds the patient of bad memories of the past, and a sound is provided to reprocess, replace or transform the bad memories.

In the present disclosure, bilateral stimulation which alternately stimulates the left and right sides of at least one part of the body through the massage device may be provided in order to stabilize the mental state of the user. To this end, the bilateral stimulation may include a massage that physically and directly stimulates at least a part of the body.

Figure 8:
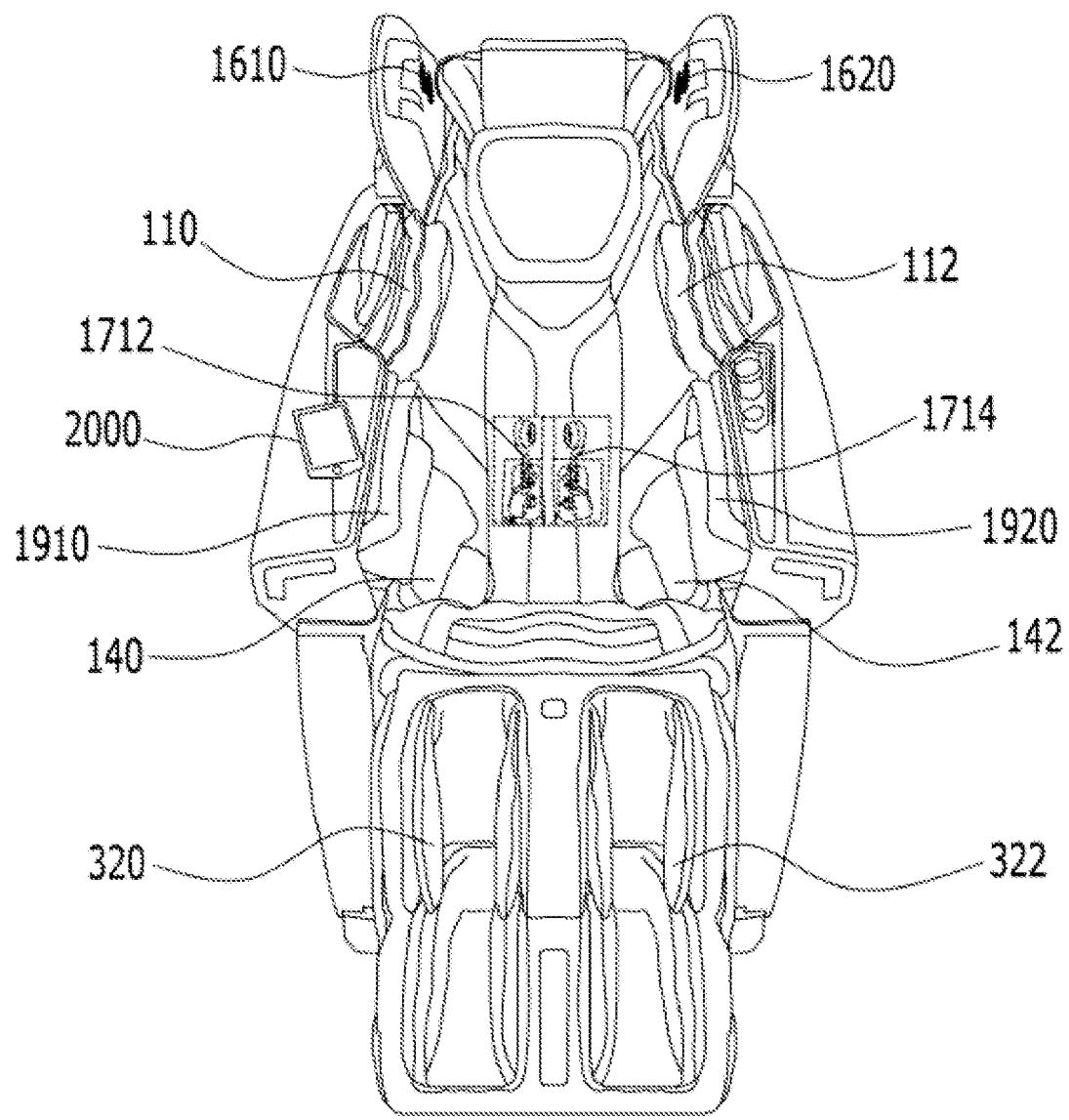
FIGS. 8 and 9 are views illustrating the massage device for providing bilateral stimulation according to the embodiment of the present disclosure.
Figure 9:
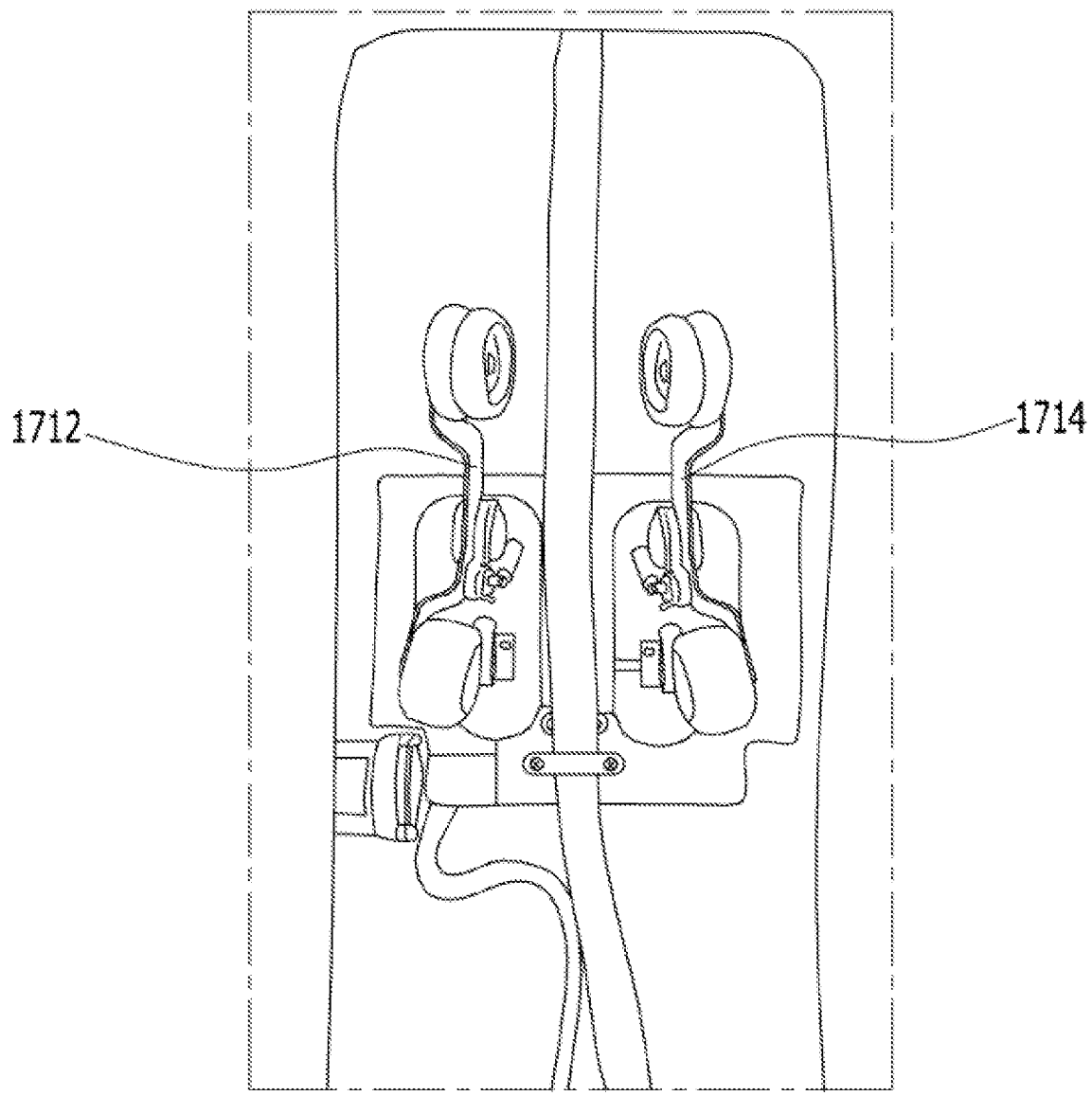

Referring to FIGS. 8 and 9, as an embodiment of the bilateral stimulation, a pair of massage modules 1712 and 1714 may alternately provide stimulation to the left and right sides of at least one of the neck, the shoulders, the backbone, the waist, the pelvis, and the hips with the backbone of the user as a central axis, and the plurality of air cells 110, 112, 1910, 1920, 140, 142, 320, and 322 may alternately provide stimulation to the left and right sides of at least one of the shoulders, the arms, the pelvis, and the legs.

In detail, the left massage module 1712 and the right massage module 1714 may provide the massage while alternately protruding, and in the plurality of air cells, the air may be alternately injected and discharged for each of the air cells on the left side and the air cells on the right side.

For example, an operation may be repeated in which the air is injected into the air cells 110, 1910, 140, and 320 corresponding to the shoulder, the arm, the pelvis, and the leg on the left side for n seconds and is then discharged from the air cells 110, 1910, 140, and 320 for m seconds, and in contrast, the air is discharged from the air cells 112, 1920, 142, and 322 corresponding to the shoulder, the arm, the pelvis, and the leg on the right side for n seconds and is then injected into the air cells 112, 1920, 142, and 322 for m seconds. In this case, the pair of massage modules 1712 and 1714 may alternately provide stimulation to the left and right sides of at least one of the neck, the shoulders, the backbone, the waist, the pelvis, and the hips with respect to the backbone of the user. A period during which the bilateral stimulation is provided through the massage modules 1712 and 1714 and a period during which the bilateral stimulation is provided through the plurality of air cells 110, 112, 1910, 1920 140, 142, 320, and 322 may differ from each other. Here, the leg air cells 320 and 322 may collectively refer to air cells provided in the leg massage part 300 corresponding to at least one of the ankle and the calf.

In providing the above-described bilateral stimulation, the massage intensity, the depth at which the massage module pushes the backbone, the strength of the air cells, and the time during which the bilateral stimulation is provided may be determined according to the level of the mental massage pattern as described above.

Figure 10:
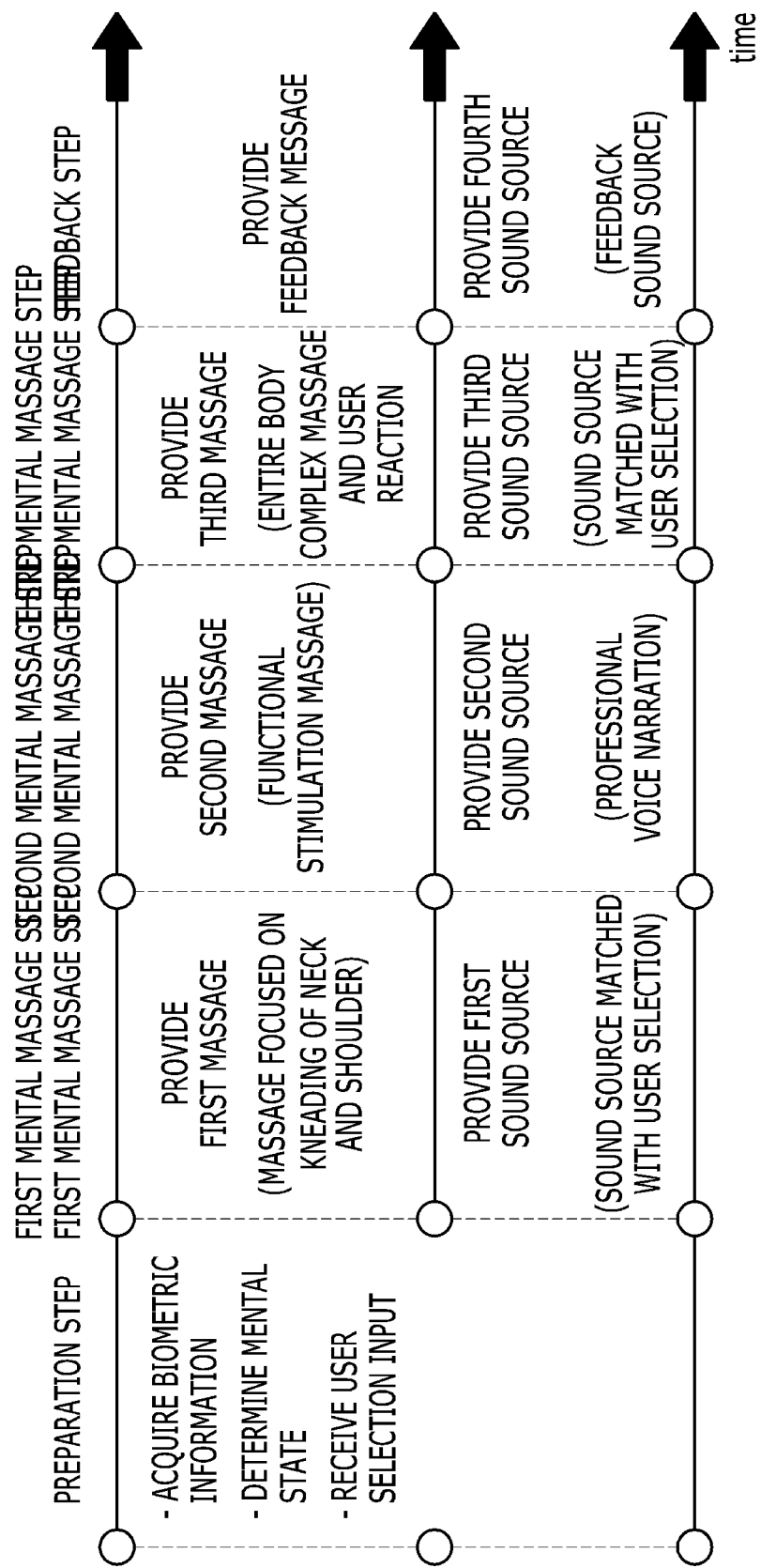
FIG. 10 is a flowchart for describing steps of providing a mental massage according to the embodiment of the present disclosure.

FIG. 10 is a flowchart for describing steps of providing a mental massage according to the embodiment of the present disclosure.

Referring to FIG. 10, the steps of providing a mental massage according to the embodiment of the present disclosure may include a preparation step, a first mental massage step, a second mental massage step, a third mental massage step, and a feedback massage step.

In the preparation step, the mental state may be determined on the basis of the biosignal of the user. For this, reference will be made to the above description of the mental state determination unit 1210. In addition, in the preparation step, a user interface which enables the user to select at least one item among a plurality items related to a emotion type and an arousal degree of a person may be provided.

Figure 11:
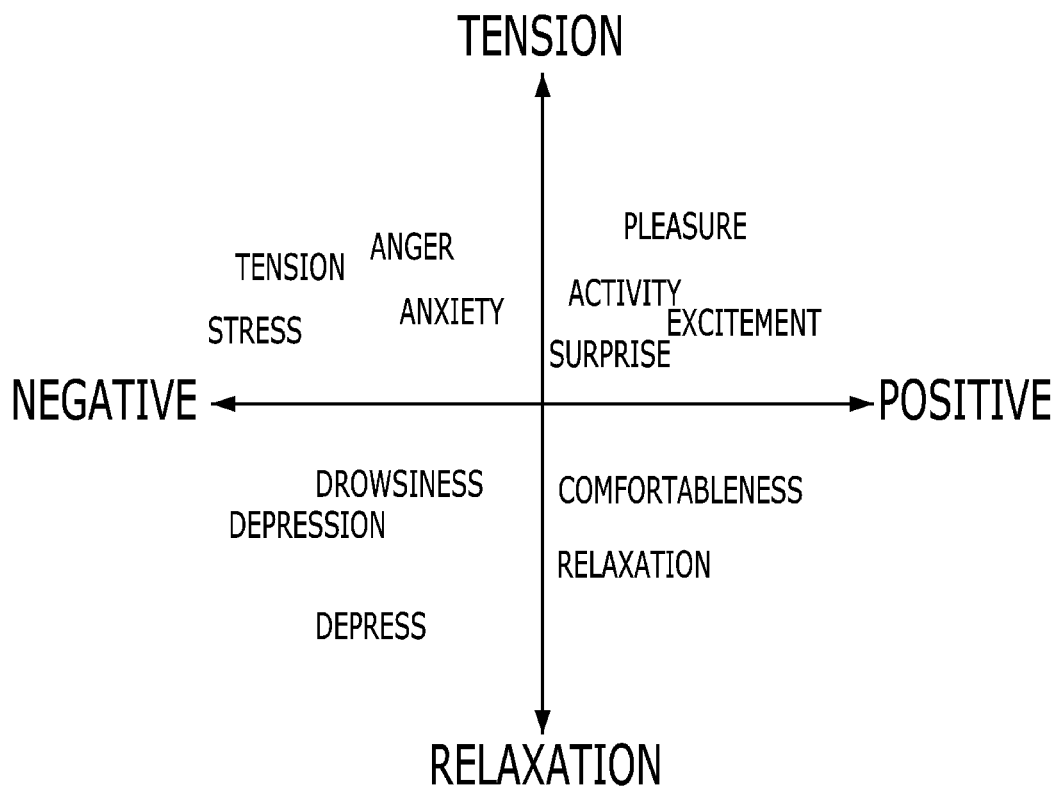
FIG. 11 illustrates an example of a user interface through which a user may select an item related to a mental state according to the embodiment of the present disclosure.

For example, an interface related to the emotion type and the arousal degree of a person may be displayed as a region display graph as illustrated in FIG. 11. Items including joy, excitement, surprise, tension, stress, anger, drowsiness, depression, relaxation, and happiness may be displayed on the graph, and the user may select at least one of the items.

A sound source matched in advance for each item may be stored in the storage unit 1500, and a sound source corresponding to the item selected by the user may be provided in at least one step among the first mental massage step to the third mental massage step. Here, the sound source matched with each item may be a sound source set to induce the emotion and the arousal degree of a person to become positive and relaxed from the emotion type and the arousal degree selected by the user.

For example, the sound sources may include information in the form of a predetermined audio, including various types of music such as classical music, jazz music, instrumental music, and pop music, natural sounds such as sounds of water and sounds of birds, and binaural beats. Further, the binaural beat in the present disclosure may mean a specific type of audio information that may control brain waves.

In this way, through the interface that allows the user to input his/her determination and intention for the mental state, the sound source desired by the user may be reproduced, and whenever the user uses the massage device, a change and a history of the selected mental state may be grasped.

In the second mental massage step, a massage including functional stimulation may be provided. For the massage including the functional stimulation, reference will be made to the above description of the bilateral stimulation according to the present disclosure.

Professional voice narration provided together with the bilateral stimulation may be related to a narrative that induces the user to try at least one of self-talk, breathing exercises, brain exercises, a thought conversion method, a meditation method, and an anxiety relaxation exercises.

For example, when the mental state of the user is determined as the fourth state (emotion state is negative and stress level is medium), the bilateral stimulation according to the present disclosure may be provided, and at the same time, a narrative for inducing self EMDR may be provided. Accordingly, physical and direct bilateral stimulation is provided to at least a part of the user's body, and at the same time, a situation similar to rapid eye movement (REM) sleep is made using the movement of the user's eyes. Thus, this may help to reprocess traumatic memories and, and thereby treat dissociation and autonomic nervous system hyperarousal.

Here, the professional voice narration may be provided on the basis of a user's voice tone. To this end, first, a user's voice may be collected through a microphone mounted on the massage device 1000 or the control device 2000, the collected user's voice may be analyzed and classified through the control unit 1200, and the professional voice narration may be provided in the classified voice tone. In the embodiment, the user's voice tone may be classified according to a preset reference range on the basis of a frequency indicating the raising and lowering of the voice.

In the embodiment, the user's voice tone may be primarily classified into a female voice and a male voice and may be secondarily classified into a low-pitched sound, a middle-pitched sound, and a high-pitched sound. This is merely an example of classifying the voice tone, and the present disclosure is not limited thereto.

Further, the professional voice narration is provided by vocalization that abundantly includes respiration, and causes direct resonance and vibration in the body, which may induce stable emotions in relation to the user's psychological stability.

In the feedback step, the mental state determination unit 1210 may determine a mental state as a user response to the mental massage pattern provided in the second mental massage step, the mental massage pattern determination unit 1220 may re-determine the mental massage pattern according to the mental state determined as the user response, and the mental massage provision unit 1230 may provide the massage according to the re-determined mental massage pattern.

The present disclosure may analyze the user's mental state changed in response to the mental massage pattern and re-determine the mental massage pattern as well as classify a mental state region of the user and provide feedback through such a feedback step, thereby providing customized bilateral stimulation precisely in consideration of the user's mental state.

Figure 12:
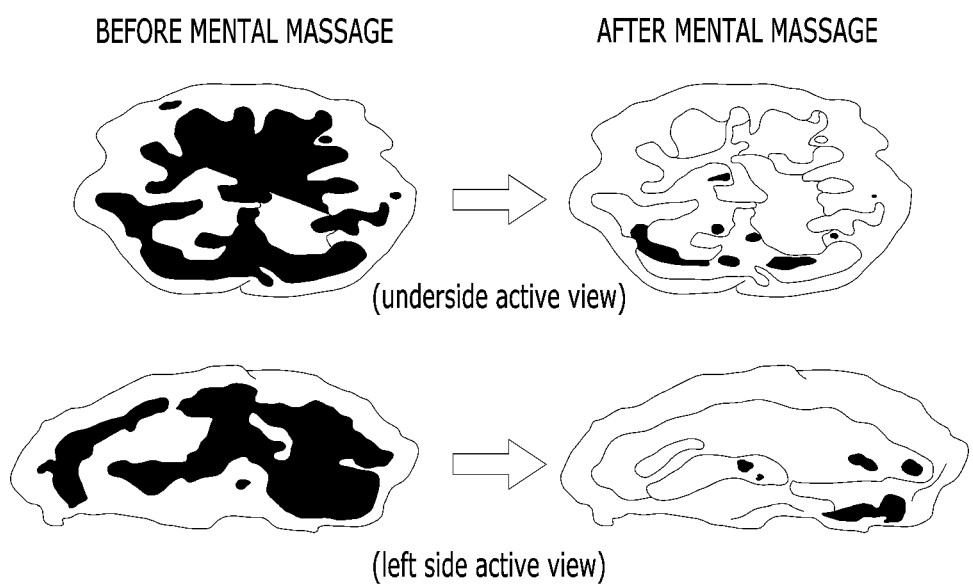
FIG. 12 is a reference diagram illustrating a brain state changed by the mental massage according to the embodiment of the present disclosure.

Referring to FIG. 12, it may be seen that the activation of the limbic system is reduced through use of the massage device that stabilizes the mental state according to the embodiment of the present disclosure. The limbic system is responsible for basic emotions and memories in the human body. Further, through use of the massage device according to the embodiment of the present disclosure, the activation of the frontal lobe may be increased, and an anterior cingulate cortex (ACC) region may be activated in relation to the emotions and memories related to thought.

Meanwhile, the massage device according to the embodiment of the present disclosure may store the histories of the mental state and the mental massage pattern for each user while providing the mental massage, and thus may observe the change and history of the mental state for each user by the massage providing bilateral stimulation.

Figure 13:
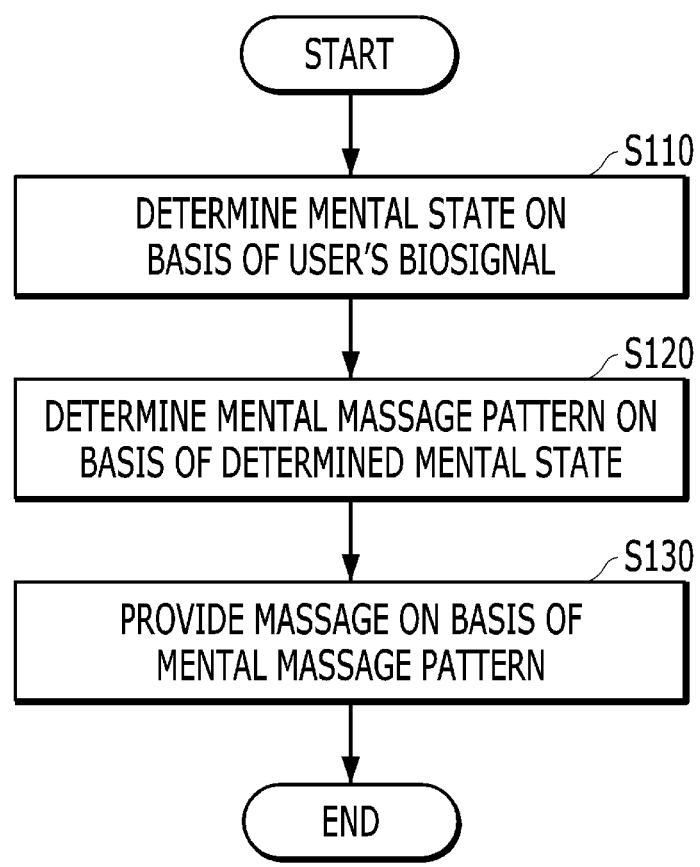
FIG. 13 is a flowchart for describing a method for providing a mental massage according to the embodiment of the present disclosure.

FIG. 13 is a flowchart for describing a method of providing a mental massage that helps to heal anxiety and depression according to the embodiment of the present disclosure.

In step S110, the massage device 1000 may determine the mental state on the basis of the user's biosignal. The method of determining the mental state on the basis of the user's biosignal by the massage device 1000 has been described in detail with reference to FIG. 1.

In step S120, the massage device 1000 may determine the mental massage pattern on the basis of the determined mental state. The method of determining the mental massage pattern by the massage device 1000 has been described in detail with reference to FIG. 3.

In step S130, the massage device 1000 may provide the massage to the user on the basis of the determined mental massage pattern. The method of providing the massage to the user on the basis of the mental massage pattern by the massage device 1000 has been described in detail with reference to FIG. 3.

Those skilled in the art will appreciate that the present disclosure may be implemented in combination with other program modules and/or as a combination of hardware and software. For example, the present disclosure may be implemented by a computer-readable medium.

Any computer-accessible medium may be a computer-readable medium, and such a computer-readable medium includes volatile and nonvolatile media, transitory and non-transitory media, and removable and non-removable media. As a non-limiting example the compute-readable medium may include a computer-readable storage medium and a computer-readable transmission medium.

The computer-readable storage medium includes the volatile and non-volatile media, the transitory and non-transitory media, and the removable and non-removable media, which are implemented by a predetermined method or technique of storing information such as a computer-readable command, a data structure, a program module, or other data. The computer-readable storage medium includes the RAM, a read-only memory (ROM), an electrically erasable and programmable read only memory (EEPROM), a flash memory, other memory technologies, a compact disc read-only memory (CD-ROM), a digital video disk (DVD), other optical disk storage devices, a magnetic cassette, a magnetic tape, a magnetic disk storage device, other magnetic storage devices, or any other medium that may be accessed by a computer and may be used to store desired information, but the present disclosure is not limited thereto.

The computer-readable transmission medium includes all information transfer media in which the computer-readable command, the data structure, the program module, other data, or the like is implemented on a modulated data signal such as a carrier wave or other transport mechanisms. The term "modulated data signal" means a signal in which one or more of characteristics of the signal are set or changed so as to encode information in the signal. As a non-limiting example, the computer-readable transmission medium includes a wired medium such as a wired network or a direct-wired connection and a wireless medium such as sound, a radio frequency (RF), an infrared ray, and other wireless media. Combinations of any of the above-described media are also included in the scope of the computer-readable transmission medium.

Those skilled in the art may understand that various exemplary logic blocks, modules, processors, means, circuits, and algorithm steps, which have been described in connection with the embodiments disclosed herein may be implemented by electronic hardware (for convenience, referred to as "software" herein), various types of programs or design code, or combinations of both thereof. In order to clearly describe this interchangeability of hardware and software, various exemplary components, blocks, modules, circuits, and steps have been described above generally in connection with their functions. Whether such functions are implemented as hardware or software depends on design constraints imposed on specific applications and the overall system. Those skilled in the art may implement the functions described in various ways for each specific application, but such implementation decisions should be not construed as deviating from the scope of the present disclosure.

Various embodiments proposed herein may be implemented as a manufacturing article using a method, a device, or a standard programming and/or an engineering technology. The term "manufacturing article" includes a computer program, a carrier, or a medium accessible from any computer-readable device. For example, the computer-readable storage medium includes magnetic storage devices (for example, hard disks, floppy disks, magnetic strips, and the like), optical disks (for example, CDs, DVDs, and the like), smart cards, and flash memory devices (for example, EEPROMs, cards, sticks, key drives, and the like), but the present disclosure is not limited thereto. The term "machine-readable medium" includes wireless channels and various other media that may store, hold, and/or transmit command (s) and/or data, but the present disclosure is not limited thereto.

It should be understood that a specific order or hierarchy of steps in the presented processes is an example of exemplary approaches. It should be understood that the specific order or hierarchy of the steps in the processes may be rearranged within the scope of the present disclosure on the basis of design priorities. The appended method claims provide elements of various steps in a sample order, but do not mean that the present disclosure is limited to the presented specific order or hierarchy.

The description of the presented embodiments is provided to enable those skilled in the art to use or implement the present disclosure. Various modifications with respect to these embodiments will be apparent to those skilled in the art, and the basic principles defined herein may be applied to other embodiments without departing from the scope of the present disclosure. Therefore, the present disclosure is not limited to the embodiments presented herein, but should be construed in the widest scope consistent with the principles and novel features presented herein.

The invention claimed is:

1. A massage device comprising:
   a mental state determination processor configured to determine a mental state on a basis of a biosignal of a user;
   a mental massage pattern determination processor that determines a mental massage pattern based on the mental state; and
   a mental massage provision processor configured to control a massage assembly to provide a predetermined pattern of massage in accordance with the mental massage pattern to the user;
   wherein the biosignal includes a first biosignal and a second biosignal, and wherein the mental state determination processor includes:
      an emotional state determination processor configured to extract a first feature from the first biosignal and determine an emotion state based on the first feature;
      a stress level determination processor configured to extract a second feature by analyzing the second biosignal and determine a stress level based on the second feature; and
      a mental state selection processor configured to select one of a plurality of mental states classified by a preset mental state model based on the emotional state and the stress level, wherein the emotional state determination processor extracts the first feature based on a signal measured through at least one of an electroencephalography (EEG) sensor, a respiration sensor, and a blood volume pulse (BVP) sensor, and the stress level determination processor extracts the second feature based on a signal measured through an electro-dermal activity (EDA) sensor, and wherein the mental state determination processor determines a strength level of the mental massage pattern based on the mental state selected by the mental state selection processor.

2. The massage device of claim 1, wherein as the strength level of the mental massage pattern corresponds to a degree of a massage intensity, a depth at which the massage assembly configured to push a backbone, a strength of an air cell of the massage assembly, and a time during which the predetermined pattern of massage is provided.

3. The massage device of claim 1, wherein the predetermined pattern of massage includes a functional stimulation having a functional stimulation massage which provides bilateral stimulation, alternately stimulating left and right sides of at least a part of the user's body.

4. The massage device of claim 1, wherein the mental massage provision processor is configured to control the massage assembly to provide the massage and, at a same time, provide professional voice narration according to the user's mental state.

5. The massage device of claim 1, further comprising a database that stores information on the mental state and information on the massage pattern for each user.

6. The massage device of claim 1, wherein the mental state determination processor determines a mental state as the user's response to the mental massage pattern, the mental massage pattern determination processor re-determines the mental massage pattern according to the mental state determined by the user's response, and the mental massage provision processor is configured to provide the massage according to the mental massage pattern, which is redetermined and provides a feedback massage.

7. The massage device of claim 1, wherein the preset mental state model is set based on both the emotional state and the stress level, with each of the emotional state and the stress level having at least two or more levels.

8. A method of providing a mental massage that helps heal anxiety and depression, the method comprising:
  determining a mental state based on a biosignal of a user;
  determining, by a mental massage pattern determination processor, a mental massage pattern based on the mental state; and
  providing, by a mental massage provision processor, a predetermined pattern of massage in accordance with the mental massage pattern, wherein the biosignal includes a first biosignal and a second biosignal, and wherein the determining of the mental state includes:
  extracting, by an emotional state determination processor, a first feature from the first biosignal and determining an emotional state based on the first feature,
  extracting, by a stress level determination processor, a second feature by analyzing the second biosignal and determining a stress level based on the second feature, and
  selecting, by a mental state selection processor, one of a plurality of mental states classified by a preset mental preset mental state model based on the emotional state and the stress level, wherein the emotional state determination processor extracts the first feature based on a signal measured through at least one of an electroencephalography (EEG) sensor, a respiration sensor, and a blood volume pulse (BVP) sensor, and the stress level determination processor extracts the second feature based on a signal measured through an electro-dermal activity (EDA) sensor, and wherein the mental state determination processor determines a strength level of the mental massage pattern based on the mental state selected by the mental state selection processor.

9. The method of claim 8, wherein the determining of the mental state includes determining the strength level of the mental massage pattern based on the mental state selected, and as the strength level of the mental massage pattern is configured to correspond to a massage intensity, a depth at which a massage assembly pushes a backbone, a strength of an air cell of the massage assembly, and a time during which the predetermined pattern of massage is provided.

10. The method of claim 8, wherein the predetermined pattern of massage includes a functional stimulation having a functional stimulation massage which provides bilateral stimulation, alternately stimulating left and right sides of at least a part of the user's body.

11. The method of claim 8, wherein the preset mental state model is set based on both the emotional state and the stress level, with each of the emotional state and the stress level having at least two or more levels.

* * * * *